US012233049B2

United States Patent
Mandge et al.

(10) Patent No.: US 12,233,049 B2
(45) Date of Patent: Feb. 25, 2025

(54) STABLE PHARMACEUTICAL COMPOSITIONS OF CLONIDINE

(71) Applicant: Slayback Pharma LLC, Princeton, NJ (US)

(72) Inventors: Shailendra Mandge, Hyderabad (IN); Harish Gunda, Nizamabad (IN); Naga Venkata Durga Prasad Ketha, Hyderabad (IN); Venkateshwar Reddy Keesara, Hyderabad (IN); Satheesh Balasubramanian, Hyderabad (IN); Sumitra Ashokkumar Pillai, Hyderabad (IN)

(73) Assignee: SLAYBACK PHARMA LLC, Princeton, NJ (US)

( * ) Notice: Subject to any disclaimer, the term of this patent is extended or adjusted under 35 U.S.C. 154(b) by 0 days.

(21) Appl. No.: 17/866,115

(22) Filed: Jul. 15, 2022

(65) Prior Publication Data
US 2023/0149359 A1 May 18, 2023

(30) Foreign Application Priority Data
Nov. 15, 2021 (IN) .............................. 202141052364

(51) Int. Cl.
| | | |
|---|---|---|
| *A61K 31/4168* | (2006.01) | |
| *A61J 1/06* | (2006.01) | |
| *A61J 1/14* | (2023.01) | |
| *A61K 9/00* | (2006.01) | |
| *A61K 47/02* | (2006.01) | |

(52) U.S. Cl.
CPC ........... *A61K 31/4168* (2013.01); *A61J 1/065* (2013.01); *A61J 1/1468* (2015.05); *A61K 9/0053* (2013.01); *A61K 47/02* (2013.01)

(58) Field of Classification Search
CPC .. A61K 9/2018; A61K 9/2027; A61K 9/2054; A61K 9/2077; A61K 9/2095; A61K 31/137; A61K 31/167; A61K 31/351; A61K 31/4453; A61K 31/485; A61K 31/53; A61K 31/5513; A61K 9/0056; A61K 9/14; A61K 9/16; A61K 9/167; A61K 9/20; A61K 9/205; A61K 31/4745; A61K 47/02; A61K 47/26; A61K 47/34; A61K 47/36; A61K 47/38; A61K 9/0004; A61K 9/0065; A61K 9/146; A61K 9/2013; A61K 9/2031; A61K 9/2059; A61K 9/282; A61K 9/2853; A61K 9/2866
See application file for complete search history.

(56) References Cited

U.S. PATENT DOCUMENTS

| | | | |
|---|---|---|---|
| 11,207,297 B2 | 12/2021 | Patel et al. | |
| 2005/0058696 A1* | 3/2005 | Donello | ................ A61K 47/02 424/449 |

FOREIGN PATENT DOCUMENTS

| | | | | |
|---|---|---|---|---|
| GB | 2548424 A | * | 6/2016 | ......... A61K 31/4168 |
| JP | 2004516099 A | * | 6/2004 | .............. A61P 27/02 |

OTHER PUBLICATIONS

JP2004516099A translation (Year: 2004).*
"Duracion"; PI-218/219-A Revised: May 2010.
A.L. De Goede, et al; "Development and validation of a paediatric oral formulation of clonidine hydrochloride"; International Journal of Pharmaceutics 433 (2012) 119-120.
Dolores Kostecka, et al; "Formulation of a Stable Parenteral Product; Clonidine Hydrochloride Injection"; PDA Journal of Pharmaceutical Science & Technology, vol. 52, No. 6 J Nov.-Dec. 1998.

* cited by examiner

*Primary Examiner* — Audrea B Coniglio
*Assistant Examiner* — Andrea Buckley
(74) *Attorney, Agent, or Firm* — Birch, Stewart, Kolasch & Birch, LLP

(57) ABSTRACT

The present invention relates to liquid pharmaceutical compositions of clonidine or its pharmaceutically acceptable salts thereof. Preferably, the liquid pharmaceutical compositions are suitable for oral administration, and are stable for extended periods of time. More specifically, stable liquid pharmaceutical compositions of clonidine at concentrations of 1 μg/mL or more are provided. The present invention further relates to stable oral liquid compositions of clonidine, methods for their administration, processes for their production, and use of these compositions for treatment of diseases treatable by clonidine.

23 Claims, No Drawings

STABLE PHARMACEUTICAL COMPOSITIONS OF CLONIDINE

CROSS-REFERENCE TO RELATED APPLICATIONS

This application claims priority to Indian Application No. IN 202141052364, filed on Nov. 15, 2021, which is incorporated herein by reference in its entirety.

FIELD OF THE INVENTION

The present disclosure relates to liquid pharmaceutical compositions of clonidine for oral administration that are stable for extended periods of time, their preparation and methods of use.

BACKGROUND OF THE INVENTION

Clonidine is an imidazole derivate which acts as a partial agonist of alpha-2 adrenoceptors in the brain stem. This action results in reduced sympathetic outflow from the central nervous system, a decrease in peripheral resistance, renal vascular resistance, heart rate, and blood pressure. The chemical name of clonidine is N-(2,6-dichlorophenyl)-4,5-dihydro-1H-imidazol-2-amine and its chemical structure is represented by the structural formula (I):

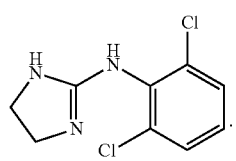

Clonidine is freely soluble in water and is classified either as Class I (high solubility/high permeability) or Class III (high solubility/low permeability) under the Biopharmaceutics Classification System. After oral administration, clonidine is almost completely absorbed from the gastrointestinal tract and is subject to rapid liver metabolism. A peak plasma level is generally reached within 3 to 5 hours; the plasma half-life is about 12 to about 16 hours and the elimination half-life is about 6 to about 24 hours.

Clonidine is known to be effective in the treatment of clinical disorders including hypertension, tourette's syndrome, prophylaxis of common migraine headaches, decreasing hyperactivity, impulsivity and overexcitability in attention deficit hyperactivity disorder (ADHD), manic states and many other clinical syndromes. In pediatrics, clonidine is frequently used in pediatric intensive care and anesthesia. Furthermore, clonidine is also used to ease withdrawal symptoms associated with the long-term use of narcotics, alcohol and nicotine (smoking) in older children and adults. Other uses are as an analgesic in neuropathic pain, in continuous epidural infusion or in severe non-treatable oncologic pain, combined with opioids. Clonidine is also used in infants to treat Neonatal Abstinence Syndrome (NAS), NAS which occurs due to fetal exposure to illicit or prescription drugs used by the mother prenatally. Such intra-uterine exposure of the fetus to drugs may lead to neonatal intoxication depending on the substance, extent of exposure and timing of exposure in relation to delivery. From 2004 to 2014, the incidence of NAS in the United States has increased to 433%, from 1.5 to 8.0 per 1,000 hospital births. NAS poses a significant public health challenge nationally, with a six-fold increase in incidence (1.2 to 6.7 per 1000 hospital births/year) from 2000-2016.

Among a range of pharmacological treatments available for NAS, opioid replacement therapy is considered as a first-line treatment. However, potential adverse effects of opioids on neonates' neurologic and cognitive development have raised serious questions. Clonidine and phenobarbital as an adjunct therapy to opioids are beneficial for decreasing the duration of opioid treatment as well as for limiting the doses of opioids required. However, compared to phenobarbital, clonidine is associated not only with fewer side effects but also a significantly shorter overall treatment duration because no dose tapering is required once treatment is completed. The administration of clonidine in infants at 0.5-1 µg/kg/6 hours, alone or in combination with other medicinal products, appears to be effective at reducing the time needed for treatment.

Commercially marketed product containing hydrochloride salt of clonidine is available in tablet form for oral administration (Catapres®) in three dosage strengths: 0.1 mg (EQ 0.087 base), 0.2 mg (EQ 0.174 base) and 0.3 mg (EQ 0.261 base). Clonidine is also available as a transdermal patch (Catapres-TTS®) for topical administration, or as an injectable form (Duraclon®) to be given epidurally, directly to the central nervous system. The dose of clonidine administered to individual patients may vary depending on the specific indication, severity of the clinical condition, body weight and renal function of the patient. The recommended oral clonidine dosing for adult and pediatric patients includes an initial dose of 0.1 mg twice daily (morning and bedtime), followed by an incremental maintenance dose of 0.1 mg per day made at weekly intervals, until the desired response is achieved. Clonidine has a narrow therapeutic index i.e., narrow window between their effective dose and toxic dose, and thus, small changes in the dosage of clonidine can potentially lead to sub-therapeutic or toxic effects.

The standard regimen of clonidine in neonates with NAS is 1 µg/kg every 4-6 hours via the nasogastric route for a period of 1 week or longer. Thus, because of its narrow therapeutic range, there is a need to adjust the dosage of clonidine according to actual blood levels of the patient. Health care professionals and caregivers manipulate the solid and injectable dosage forms of clonidine, a process referred to as compounding, in order to cater to the needs of adult and pediatric patient population. However, such manipulated dosage forms fall outside the regulatory agency approval process and are associated with safety and efficacy concerns. Secondly, healthcare professionals are mostly unaware of the stability of these preparations. Due to this gap in knowledge, healthcare professionals must prepare such admixtures multiple times a day when the treatment is indicated, resulting in increased workload and the risk of treatment errors. Additionally, such compounding practices use time, money, and resources that could be directed to other aspects of pharmacy-related patient care if commercially available formulations were available. Furthermore, pharmacy practice of dispensing extemporaneous preparations from solid formulations causes medication errors, adverse events and fatal conditions especially for the drug like clonidine which falls in narrow therapeutic index category.

Thus, there is a need to develop a ready-to-administer oral liquid composition of clonidine which would not only minimize the risk of potential compounding errors, but also reduces the associated costs. In addition, bulk preparation would save nursing time and avoid delays in timely administration of clonidine.

Liquid compositions such as oral suspensions have drawbacks pertaining to physical stability (sedimentation and compaction) and poses a challenge for uniform and accurate dosing. Thus, it is desirable for the composition of the present invention to be in the form of oral solution, so as to avoid the drawbacks invited by oral suspension formulation.

Furthermore, it is also desirable for inventive clonidine compositions suitable for oral administration to remain stable over extended periods of time under suitable storage conditions. Miriam et.al (Stability of an extemporaneously compounded clonidine hydrochloride oral liquid; AJHP Vol 49 January 1992, Pg. 122-125) discloses that the stability of extemporaneously compounded liquid preparation of clonidine hydrochloride in Simple Syrup, NF, made from crushed tablets of Catapres®, is stable for 28 days when stored in amber glass bottles under refrigeration at 4° C. Such manipulated dosage forms have a very short shelf life at room temperature and thus need for refrigeration is a must.

Thus, it is desirable to develop novel stable liquid compositions of clonidine suitable for oral administration to human subjects, which are ready-to-administer, which allow flexibility in administration of doses, which are therapeutically effective, and exhibit prolonged room temperature stability without any significant loss of potency enabling optimal usage of clonidine compositions.

The present invention fulfils this need by developing stable oral liquid compositions of clonidine to achieve an improved standard of patient care.

SUMMARY OF THE INVENTION

In one aspect, the present invention provides a multi-dose liquid oral pharmaceutical composition having extended stability, said composition comprising: clonidine hydrochloride at a concentration of about 20 µg/mL; at least one pharmaceutically acceptable vehicle; at least one stabilizer; and at least one preservative; wherein said composition is stable for at least 6 months when stored at 25° C./60% RH.

In another aspect, the present invention provides a multi-dose liquid oral pharmaceutical composition having extended stability, said composition comprising: clonidine hydrochloride at a concentration of about 20 µg/mL; at least one pharmaceutically acceptable vehicle; at least one stabilizer; and at least one preservative; wherein said composition stable for at least 6 months when stored at 40° C./25% RH and/or 40° C./75% RH.

The composition as described above, wherein the level of total impurities is less than about 2% (w/w) as measured by HPLC, when stored at 25° C./60% RH or 40° C./25% RH or 40° C./75% RH for at least 6 months.

In one aspect, the present invention provides a multi-dose liquid pharmaceutical composition having extended stability suitable for oral administration comprising: (a) clonidine hydrochloride at a concentration of about 20 µg/mL; (b) at least one pharmaceutically acceptable vehicle; (c) at least one stabilizer; and (d) at least one preservative other than methyl para-hydroxybenzoate; wherein said composition is stable for at least 6 months when stored at 25° C./60% RH.

The composition as described above, wherein the level of total impurities is less than about 2% (w/w) as measured by HPLC, when stored at 25° C./60% RH for at least 6 months.

The composition as described above, wherein the composition exhibits in-use shelf life of at least one month when stored at room temperature.

The compositions as described above, wherein said compositions are stable for at least 6 months when stored at 40° C./75% RH or 40° C./25% RH or 30° C./25% RH or 25° C./60% RH or 25° C./40% RH conditions.

In another aspect, the present invention provides a multi-dose liquid oral pharmaceutical composition having extended stability comprising: (a) therapeutically effective amount of clonidine hydrochloride; (b) sodium chloride as a stabilizer; and (c) purified water, wherein the composition is free of buffer, wherein said composition is stable for at least 6 months when stored at 25° C./60% RH.

In another aspect, the present invention provides a multi-dose liquid oral pharmaceutical composition having extended stability comprising: (a) clonidine hydrochloride at a concentration of about 20 µg/mL; (b) sodium chloride as stabilizer; and (c) purified water, wherein the composition is paraben-free, wherein said composition is stable for at least 6 months when stored at 25° C./60% RH.

The composition as described above, wherein the pharmaceutically acceptable liquid vehicle is selected from group consisting of water, purified water, alcohol, glycol, dimethyl sulfoxide, ringer's solution, isotonic sodium chloride solution, glycerine or mixtures thereof.

The composition as described above, wherein said composition has a pH in a range from about 4 to about 8.

The composition as described above, wherein said composition has a pH in a range from about 5 to about 6.

The composition as described above, wherein the stabilizer is sodium chloride and the preservative is potassium sorbate and/or sodium propionate.

The composition as described above, wherein the composition is a solution.

In certain aspects as described above, the composition as described is a said composition is a ready-to-administer (RTA) or safe-to-administer (STA) clonidine compositions suitable for oral administration, wherein said composition has extended stability.

In another aspect, the present invention provides a stable buffer-free liquid compositions of clonidine, suitable for oral administration, wherein clonidine is present at a concentration of about 20 µg/mL.

In another aspect, the present invention provides a stable paraben-free liquid compositions of clonidine, suitable for oral administration, wherein clonidine is present at a concentration of about 20 µg/mL.

In another aspect, the present invention provides a stable buffer-free and paraben-free liquid compositions of clonidine, suitable for oral administration, wherein clonidine is present at a concentration of about 20 µg/mL.

In another aspect, the present invention provides a process for preparing a stable solution suitable for oral administration comprising clonidine, wherein the inventive process comprises dissolving clonidine in a purified water along with a stabilizer.

In certain aspects as described above, the pharmaceutical composition is contained in single-dose and/or multi-dose container. In one aspect, the composition may be contained in bottles or blow-fill seals vials. In some aspects, the bottles may be made from clear glass, amber glass, or plastic. In some aspects, the bottles may be in the range of about 0.1 mL to 500 mL in volume.

In certain embodiments as described above, the composition has prolonged room temperature stability, wherein said stability is defined as absence of significant loss in potency.

The composition as described above, wherein said composition retains at least 90% of the potency of clonidine when stored at 40° C./75% RH or 40° C./25% RH for at least 6 months.

The composition as described above, wherein said composition retains at least 90% of the potency of clonidine when stored at 25° C./60% RH or 25° C./40% RH for at least 6 months.

The composition as described above, wherein the amount of total impurities in said composition is less than about 2% (w/w) as measured by HPLC.

The composition as described above, wherein any unknown impurity in said composition is less than about 1% (w/w) as measured by HPLC.

The composition as described above, wherein any known impurity in said composition is less than about 1% (w/w) as measured by HPLC.

The composition as described above, wherein said composition is provided in a polyethylene terephthalate (PET) bottle.

The composition as described above, wherein said composition is provided in a high-density polyethylene (HDPE) bottle.

The composition as described above, wherein said composition is provided in a glass bottle.

DETAILED DESCRIPTION OF THE INVENTION

Unless defined otherwise, all the technical and scientific terms used herein have the same meaning as commonly known by a person skilled in the art. In case of conflict, the definitions provided herein will prevail. Unless specified otherwise, all the percentages, portions and ratios in the present invention are on a weight/weight (w/w) basis.

As used herein, the term "about" means having a value falling within an accepted standard of error of the mean when considered by one of ordinary skill in the art. Frequently, the term "about" refers to ±20%, preferably ±10%, and more preferably ±5% of the value or range to which it refers. However, when the term "about" is used in connection with pH, it should be considered as ±2 units of the pH value.

When referring to clonidine, unless otherwise specified or apparent from context it is understood that the inventors are also referring to the pharmaceutically acceptable salts of clonidine. One well-known commercially available salt for clonidine is its hydrochloride salt. Some other examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like. However, clonidine in the form of its hydrochloride salt is the most preferred commercially available form.

The term "pharmaceutically acceptable" substances mean those substances which, according to common medical judgment are suitable to be in contact with a tissue of a patient without any inappropriate toxicity, irritation, allergic response, etc., have a reasonable balance between advantages and disadvantages, and can be applied to its target use effectively.

The term "pharmaceutically acceptable salt" refers to salts which are formed with inorganic or organic acids.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The terms "pharmaceutical composition," "pharmaceutical product," "pharmaceutical dosage form," "dosage form," "composition", "formulation", etc., refer to a pharmaceutical composition administered to a patient in need of treatment, including but not limited to tablet, hard-gelatin capsule, soft-gelatin capsule, oral suspension, oral solution, enteric coated hard-gelatin capsule, enteric coated soft-gelatin capsule, to cores, coated cores, pellets, micro pellets, pills, compressed tablets, granules, spheres, capsules, powder for suspension, powder for solution and the like.

The terms "liquid pharmaceutical composition," or "liquid composition" refer to a pharmaceutical composition administered to a patient in need of treatment, including solution or suspension.

The terms "effective amount" or "therapeutically effective amount" refer to the amount of a drug sufficient to treat, prevent, or ameliorate a condition in a subject or patient. The effective amount of clonidine or pharmaceutically acceptable salt thereof, used to practice the present invention for therapeutic management of a condition may be determined and adjusted by a person of ordinary skill to provide the appropriate amount and dosage regimen, e.g., depending upon one or more of the manners of administration, the age, body weight, sex, and/or general health of the patient.

The term "subject" refers to an animal, including a human or non-human. The terms patient and subject may be used interchangeably herein.

Within the context of this invention, the term "solution" refers to a mixture of one or more substances dispersed molecularly (i.e., dissolved) in a dissolving liquid medium or vehicle. The solution is preferably homogeneous, in the sense that active ingredient is essentially uniformly distributed and concentrated in the solution. The liquid solution may be viscous (such as syrup) or not. As already mentioned, a liquid solution differs from a suspension which comprises solid particles dispersed throughout a liquid phase in which they are not soluble.

The terms "stable" or "stability" mean that the evolution of the product with time and/or under specific environmental conditions (i.e., temperature, humidity, etc.) has no significant effects on its quality, safety and/or efficacy for a given time period. It can be measured through the formation of degradation products (impurities), variation of pH, appearance (precipitation), microbial growth, and/or color. The term "stable" indicates both chemical and physical stability. The term "stable" can further mean no more than about 10% loss of clonidine under typical commercial storage conditions. Preferably, formulations of the present inventions will have no more than about 5% loss of clonidine, no more than about 3% loss of clonidine, more preferably, no more than about 2% loss of clonidine, and more preferably, no more than about 1.5% loss of clonidine under typical commercial storage conditions (i.e., 40° C./75% RH and 40° C./25% RH and 30° C./25% RH and 25° C./60% RH and 25° C./40% RH) for at least 3 months, at least 6 months, at least 9 months, at least 12 months, at least 15 months, at least 18 months, at least 21 months, at least 24 months, at least 30 months and at least 36 months.

The term "shelf life" means the period beginning from the manufacture of a formulation and ending at a time after which the formulation cannot be expected beyond reasonable doubt to yield the therapeutic outcome approved by a government regulatory agency.

The term "shelf life after first use" or "in-use shelf life", is a period of time during which a multi-dose product can be used whilst retaining quality within an accepted specification once the container is first opened.

The multi-dose compositions can be manufactured via procedures that are well known to those skilled in the art. However, once the packaging of the product is opened, such that the composition contained therein is exposed to the atmosphere and other sources of potential microbial contamination (e.g., the hands of a human patient), the sterility of the product may be compromised. Such products are typically utilized multiple times by the patient, and are therefore frequently referred to as being "multi-dose" in nature.

Due to the frequent, repeated exposure of multi-dose products to the risk of microbial contamination, it is necessary to employ a means for preventing such contamination from occurring. The means employed may be: (i) a chemical agent that prevents the proliferation of microbes in a composition, which is referred to herein as a "preservative"; or (ii) a packaging system that prevents or reduces the risk of microbes reaching a pharmaceutical composition within a container.

The term "any person" refers to any human being capable of administering a dose of clonidine composition, including physicians, healthcare professionals, nurses, pharmacists, pharmacy technicians and patients.

"Bioequivalence" refers to the absence of a significant difference between the bioavailability, i.e., the mean ratio of AUC (over 24 hours) and the mean ratio of $C_{max}$ is within 80% to 125% between two pharmaceutical drug products (e.g., a test composition and a reference composition) over the course of a period of time, at the same dose and under the same conditions. The determination of whether or not a test composition is bioequivalent to a reference composition is determined by performing a study, referred to as a bioequivalence or comparative bioavailability study, in a group of subjects under controlled conditions.

The term "prolonged duration" as used herein refers to the holding of a composition under controlled or uncontrolled conditions for a period of more than 30 days.

The term "significant loss of potency" as used herein means no more than about 10% loss of clonidine under typical commercial storage conditions.

As used herein, the term "substantially free" of a material refers to an oral solution where the material is present in an amount of less than 0.2% w/w, less than 0.1% w/w, less than 0.02% w/w, or less than 0.01% w/w in the oral solution.

In the embodiments as described above, the liquid pharmaceutical composition will be provided in a dosage form that is suitable for oral administration including but not limited to: a solution, syrup, or elixir, wherein said pharmaceutical compositions are formulated according to conventional pharmaceutical practice.

The present invention relates to stable liquid pharmaceutical compositions of clonidine HCl at concentrations higher than 1 μg/mL concentration, and methods of preparing such solutions. In particular, the present invention provides stable liquid pharmaceutical compositions of clonidine HCl for oral administration at concentrations of about 1 μg/mL, about 5 μg/mL, about 10 μg/mL, about 15 μg/mL, about 20 μg/mL, about 30 μg/mL, about 40 μg/mL, about 50 μg/mL, about 75 μg/mL, about 100 μg/mL, about 150 μg/mL, 200 μg/mL, about 250 μg/mL, about 300 μg/mL, about 350 μg/mL, about 400 μg/mL, about 450 μg/mL and about 500 μg/mL, most preferably about 20 μg/mL.

In another embodiment, the present invention provides stable liquid pharmaceutical compositions suitable for oral administration, wherein the composition comprises (i) clonidine HCl, (ii) at least one pharmaceutically acceptable liquid vehicle, and (iii) one or more pharmaceutically acceptable excipients.

Another embodiment provides a method for treating and/or preventing hypertension in human subjects, comprising administering the compositions of the present invention as described herein.

Yet another embodiment provides a method for treating and/or preventing neonatal abstinence syndrome (NAS), tourette's syndrome, migraine, headaches, recurrent vascular headaches, attention deficit hyperactivity disorder (ADHD) and vasomotor conditions associated with menopause and characterized by flushing, comprising administering the compositions of the present invention as described herein.

The terms "pharmaceutically acceptable liquid vehicle" or "liquid vehicle" as used herein, is any liquid medium used for dilution or dissolution of parenteral, oral or peroral formulations, such as water, aqueous organic solvent, non-aqueous organic solvent and other liquids described herein or used in the pharmaceutical and/or food industry. The liquid vehicle of the present invention is selected from water, alcohols, glycols, dimethylacetamide N-methylpyrolidone, dimethyl sulfoxide, ringer's solution, isotonic sodium chloride solution, glycerine, alcohols, propylene glycol, polyethylene glycol, or their mixtures thereof. Preferably, purified water is used as a liquid vehicle.

The amount of the liquid vehicle that can be included in the compositions of the present invention is not particularly limited. Of course, when such compositions are administered to a patient, the amount of a given liquid vehicle is limited to a bio-acceptable amount, which is readily determined by one skilled in the art. However, in a preferred embodiment, the liquid vehicle of present invention is at least 80%, preferably at least 90%, and more preferably at least 99% of total composition.

In one embodiment, the present invention provides stable liquid pharmaceutical compositions suitable for oral administration comprising (i) clonidine HCl at a concentration of 1 μg/mL or more, (ii) at least one pharmaceutically acceptable liquid vehicle, and (iii) one or more pharmaceutically acceptable excipients selected from stabilizers, pH adjusting agents, buffering agents, thickening agents, anti-oxidants, chelating agents, preservatives, flavoring agents, sweetening agents, coloring agents and mixtures thereof.

In one embodiment, the present invention provides stable liquid pharmaceutical compositions suitable for oral administration comprising (i) clonidine HCl at a concentration of 1 μg/mL or more, (ii) at least one pharmaceutically acceptable liquid vehicle, (iii) one or more stabilizer, and (iv) one or more other pharmaceutically acceptable excipients selected from pH adjusting agents, buffering agents, thickening agents, anti-oxidants, chelating agents, preservatives, flavoring agents, sweetening agents, coloring agents and mixtures thereof.

In one embodiment, the present invention provides stable liquid pharmaceutical compositions suitable for oral administration comprising (i) clonidine HCl at a concentration of about 10 μg/mL, (ii) at least one pharmaceutically acceptable liquid vehicle, (iii) one or more stabilizer, and (iv) one or more pharmaceutically acceptable excipients selected from pH adjusting agents, buffering agents, thickening agents, anti-oxidants, chelating agents, preservatives, flavoring agents, sweetening agents, coloring agents and mixtures thereof.

In one embodiment, the present invention provides stable liquid pharmaceutical compositions suitable for oral administration comprising (i) clonidine HCl at a concentration of about 20 µg/mL, (ii) at least one pharmaceutically acceptable liquid vehicle, (iii) one or more stabilizers, and (iv) one or more pharmaceutically acceptable excipients selected from pH adjusting agents, buffering agents, thickening agents, anti-oxidants, chelating agents, preservatives, flavoring agents, sweetening agents, coloring agents and mixtures thereof.

In another embodiment, the present invention provides stable liquid compositions suitable for oral administration comprising (i) clonidine HCl, (ii) at least one pharmaceutically acceptable liquid vehicle, (iii) one or more stabilizers, and (iv) one or more pharmaceutically acceptable excipients selected from pH adjusting agents, buffering agents, thickening agents, anti-oxidants, chelating agents, preservatives, flavoring agents, sweetening agents, coloring agents and mixtures thereof; wherein the concentration of the stabilizer ranges from 0.001% to 20%, preferably 0.01% to 15.0%, more preferably 0.1% to 10.0%, based on total weight of the composition.

The term "stabilizer" as used herein inhibits, prevents, slows down, or reduces the degradation of clonidine. More specifically, the stabilizers of the present invention include amino acids, inorganic salts, ethylenediaminetetraacetic acid (EDTA), metal ions, cyclodextrins, sugars, sugar alcohols, monosaccharides, disaccharides or polysaccharides or combinations thereof. In certain embodiments as described herein, the concentration of the stabilizer ranges from 0.001% to 20% w/w, preferably 0.01% to 15.0% w/w, more preferably 0.1% to 10.0% w/w, based on total weight of the composition. In the embodiments as described herein, the weight ratio of clonidine hydrochloride to stabilizer ranges from about 1:50 to about 1:150, preferably 1:125.

In one embodiment, the amino acid stabilizer can be selected from, but not limited to, glycine, alanine, glutamate, sodium glutamate, arginine lysine, cysteine or methionine or mixtures thereof.

In another embodiment, the inorganic salt stabilizer can be selected from, but not limited to, sodium chloride, potassium chloride, calcium chloride, or magnesium chloride or mixtures thereof.

In another embodiment, the metal ion stabilizer can be selected from, but not limited to, zinc, magnesium and calcium or mixtures thereof.

In one embodiment, the cyclodextrin stabilizer can be selected from, but not limited to, cyclodextrin, α-cyclodextrin, β-cyclodextrin, δ-cyclodextrin, γ-cyclodextrin, or combinations thereof.

In one embodiment, the stabilizer is a sugar. In one embodiment, the sugar is selected from, but not limited to, sucrose, mannitol or trehalose or mixtures thereof. In another embodiment, the stabilizer can be selected from, but not limited to, monosaccharides such as glucose, galactose, fructose, or mannose; disaccharides such as sucrose, maltose, or lactose; polysaccharides such as oligosaccharides, starch, cellulose, or mixtures thereof.

In yet another embodiment, the stabilizer is a sugar alcohol selected from erythritol, threitol, arabitol, xylitol, ribitol, mannitol, sorbitol, dulcitol, iditol, isomalt, maltitol, lactitol, polyglycitol or combinations thereof.

Further, the compositions of the present invention optionally comprise one or more pharmaceutically acceptable excipients selected from pH adjusting agents, buffering agents, thickening agents, anti-oxidants, chelating agents, preservatives, flavoring agents, sweetening agents, coloring agents and mixtures thereof.

In addition to stabilizing pharmaceutical preparations against chemical and physical degradation, multi-dose pharmaceutical preparations must usually be protected from microbial contamination. Aqueous solutions, syrups, emulsions and suspensions are often susceptible to microorganisms such as molds, yeasts and bacteria (eg *Pseudomonas aeruginosa*), *E. coli* (*E. Coli*), *Salmonella* spp., *Staphylococcus aureus, Candida albicans*, and *Aspergillus niger*. Contamination with these microorganisms can occur during manufacture or when a dose is taken from a multi-dose formulation. Microbial growth can also occur when sufficient water is present in the formulation. In specific embodiments, the oral liquid solution of the present invention is packaged in a glass or plastic bottle configured for use to administer multiple doses of clonidine.

In specific embodiments, the oral liquid solution of the present invention, while packaged in a container, is free from microbial contamination for a specified period of time (e.g., 20 days, 30 days, 60 days, 90 days, 180 days, 12 months, or 24 months) when tested according to <1111>USP-30 NF-25.

In specific embodiments, the oral liquid solution of the present invention, while packaged in a container, is essentially free from microbial growth for at least 24 months under storage conditions.

In specific embodiments, the oral liquid solution of the present invention, while packaged in a container, is essentially free from *Escherichia coli* (*E. coli*) for at least 24 months under standard storage conditions.

In specific embodiments, the oral liquid solution of the present invention, while packaged in a container, is essentially free from *Burkholderia cepacian* complex for at least 24 months under standard storage conditions.

In an embodiment, the present invention provides a stable multi-dose liquid pharmaceutical composition suitable for oral administration comprising (i) clonidine or its pharmaceutically acceptable salts present at a concentration of about 20 µg/mL; (ii) at least one stabilizer; (iii) at least one preservative; and (iv) at least one pharmaceutically acceptable excipient.

In one embodiment, the pharmaceutical composition of the present invention comprises a preservative selected from benzoic acid, ethanol, isopropanol, methanol, butyl alcohol, benzalkonium chloride, benzyl alcohol, cetylpyridinium chloride, chlorobutanol, chlorocresol, cresol, dehydroacetic acid, phenol, phenylethyl alcohol, phenylmercuric acetate, phenylmercuric nitrate, potassium benzoate, potassium sorbate, sodium benzoate, sodium dehydroacetate, sodium propionate, sorbic acid, thimerosal, thymol, or combinations thereof. In a preferred embodiment, the concentration of the preservative ranges from 0.001% to 10%, preferably 0.01% to 5.0%, more preferably 0.05% to 1.0%, based on total weight of the composition. In an embodiment, the weight ratio of clonidine hydrochloride to preservative ranges from about 1:20 to about 1:70, preferably 1:50.

In an embodiment, the present invention provides a stable oral solution comprising (a) clonidine HCl at a concentration of about 1 µg/mL or more; (b) pharmaceutically acceptable liquid vehicle; (c) at least one stabilizer; d) at least one preservative; and e) one or more other pharmaceutically acceptable excipients selected from pH adjusting agents, buffering agents, thickening agents, anti-oxidants, chelating agents, flavoring agents, sweetening agents, coloring agents and mixtures thereof.

In an embodiment, the present invention provides a stable oral solution comprising (a) clonidine HCl at a concentration of about 10 μg/mL; (b) pharmaceutically acceptable liquid vehicle; (c) at least one stabilizer; d) at least one preservative; and e) one or more other pharmaceutically acceptable excipients selected from pH adjusting agents, buffering agents, thickening agents, anti-oxidants, chelating agents, flavoring agents, sweetening agents, coloring agents and mixtures thereof.

In an embodiment, the present invention provides a stable oral solution comprising (a) clonidine HCl at a concentration of about 20 μg/mL; (b) pharmaceutically acceptable liquid vehicle; (c) at least one stabilizer; d) at least one preservative; and e) one or more other pharmaceutically acceptable excipients selected from pH adjusting agents, buffering agents, thickening agents, anti-oxidants, chelating agents, flavoring agents, sweetening agents, coloring agents and mixtures thereof.

Yet another class of preservatives is para-hydroxybenzoic acids, known as parabens. They are the most widely used preservative systems and have been used safely and effectively for over 20 years. However, parabens contain possible human carcinogens. The pharmaceutical compositions of the present invention are optionally paraben-free compositions. The term "paraben-free" or "free of paraben" in the context of this invention means that the present compositions and methods do not comprise the use of parabens as preservatives. In certain composition embodiments as described above, said composition does not contain or use parabens as a preservative, and more specifically, said composition does not contain methyl para-hydroxybenzoate as a preservative.

The formulation studies as disclosed herein address the need to provide liquid formulations of clonidine hydrochloride that are devoid of non-friendly—particularly to the pediatric population—excipients such as parabens, while at the same time displaying excellent physicochemical stability during storage. It was surprisingly found that the addition of parabens was not required for the production of a physicochemically stable composition of clonidine hydrochloride. The absence of paraben is highly desired in oral pharmaceutical formulations, especially formulations intended for use in pediatric formulations, as their presence may raise additional safety concerns.

The oral aqueous pharmaceutical solutions of clonidine hydrochloride of the present invention exhibit excellent in-use shelf life (i.e. shelf life after first use) when supplied in multi-dose containers. Specifically, they remain physicochemically stable and at the same time are effectively preserved when stored at room temperature (20° C.-25° C.) even when the containers are opened at least once a day for at least one month.

In an embodiment, the present disclosure provides a stable oral solution comprising (a) clonidine HCl at a concentration of about 20 μg/mL; (b) a pharmaceutically acceptable liquid vehicle; (c) at least one stabilizer; and d) one or more other pharmaceutically acceptable excipients selected from pH adjusting agents, thickening agents, anti-oxidants, chelating agents, buffering agents, flavoring agents, sweetening agents, coloring agents and mixtures thereof, wherein said solution is free of parabens.

In an embodiment, the present disclosure provides a stable pharmaceutical solution for oral use comprising: (a) clonidine hydrochloride; (b) sodium chloride as stabilizer; (c) potassium sorbate as preservative; (d) purified water; wherein the solution is free of parabens.

The term "sweetening agent" as used herein refers to both bulk (caloric) and intense (non-caloric) sweeteners, which impart sweet taste to the preparation. Examples of bulk sweeteners are dextrose, fructose, glucose, hydrogenated glucose syrup, isomalt, maltitol, maltose, mannitol, sorbitol, sucrose, xylitol, ribose, deoxyribose, neuraminic acid and mixtures thereof. Examples of intense sweeteners are acesulfame, alitame, aspartame, cyclamate, dihydrochalcone sweetener, monellin, neohesperidin, neotame, saccharin, stevioside, sucralose, the pharmaceutically acceptable salts thereof such as sodium or calcium saccharin, acesulfame potassium or sodium cyclamate, and mixtures thereof. In one embodiment, the pharmaceutically acceptable sweetener as described herein is sucralose. The concentration of the sweetening agent as described herein ranges from 0.001% to 10%, preferably 0.01% to 5.0%, more preferably 0.05% to 1.0%, based on total weight of the composition.

The term "flavoring agent" as used herein refers to an agent or a mixture of agents that adds flavor to the composition. Flavoring agent may be a natural flavor, an artificial flavor, or a mixture thereof. Flavoring agents include, but are not limited to, mint, peppermint, cola, apple, vanilla, orange, peach, apricot, raspberry, cherry, honey, lemon, coconut, pineapple, strawberry, banana, mixed berry, mixed red fruit and cream flavors and mixture thereof. In a specific embodiment, the flavoring agent of the present invention is mixed berry flavor. The concentration of flavoring agent ranges from 0.001% to 10%, preferably 0.01% to 5.0%, more preferably 0.05% to 1.0%, based on total weight of the composition.

In certain embodiments, the pharmaceutical compositions of the disclosure contain an anti-oxidant. The term "anti-oxidant" as used herein, refers to an agent which inhibits oxidation and thus is used to prevent the deterioration of the compositions by the oxidative process. Such compounds include by way of example and without limitation: sodium bisulfate, ascorbic acid, ascorbyl palmitate, glycine, L-cysteine hydrochloride, L-methionine, butylated hydroxy anisole, butylated hydroxytoluene, hydro phosphorous acid, monothioglycerol, propyl gallate, sodium ascorbate, sodium citrate anhydrous, sodium citrate dihydrate, sodium sulfide, sodium sulfite, sodium bisulfite, sodium formaldehyde sulfoxylate, thioglycolic acid, sodium metabisulfite, alpha-tocopherol and others known to those of ordinary skill in the art. The concentration of anti-oxidant in the present invention ranges from 0.001% to 10%, preferably 0.01% to 5.0%, more preferably 0.05% to 1.0%, based on total weight of the composition.

In an embodiment, the pharmaceutical compositions of the present invention can be formulated at any suitable pH using pH adjusting agent. In an embodiment, suitable pH adjusting agents include acetic acid, ammonia solution, strong; acetic acid, glacial; ammonium carbonate, anhydrous; diethanolamine; potassium hydroxide; fumaric acid; sodium bicarbonate; hydrochloric acid; sodium borate; sodium carbonate; malic acid; trolamine; phosphoric acid; sodium hydroxide; nitric acid; phosphoric acid, diluted; propionic acid; sulfuric acid.

In one embodiment the normality of the pH adjusting agent is preferably maintained in the range of between 0.01 N and 5N, preferably between 0.05N and 3N. In another embodiment the molarity of the pH adjusting agent is preferably maintained in the range between 0.01 M and 5M, preferably between 0.05M and 3M. In a preferred embodiment, the pharmaceutically acceptable pH adjusting agent of the present invention is hydrochloric acid. In particular, the concentration of the pH adjusting agent in the present invention ranges from 0.001% to 30%, preferably 0.01% to 20%, more preferably 0.05% to 15%, based on total weight of the composition.

In certain embodiments, the pharmaceutical compositions of the present invention contain a buffer. The term "buffer" or "buffering agent" as used herein, is an agent used to resist change in pH upon dilution or addition of acid or alkali. Such compounds include, by way of example and without limitation, sodium dihydrogen phosphate monohydrate, disodium hydrogen phosphate anhydrous, citric acid, ascorbic acid, acetic acid, sodium acetate, adipic acid, benzoic acid, sodium benzoate, sodium citrate, monobasic sodium phosphate, dibasic sodium phosphate, disodium hydrogen phosphate dodecahydrate, lactic acid, tris buffer, tartaric acid, potassium metaphosphate, potassium phosphate, monobasic sodium acetate, sodium bicarbonate, sodium ascorbate anhydrous, sodium ascorbate monohydrate, sodium tartrate and others known to those of ordinary skill in the art. In an embodiment the concentration of buffer in the present invention ranges from 0.001% to 10%, preferably 0.01% to 5.0%, more preferably 0.05% to 1.0%, based on total weight of the composition. In some embodiments as described herein, the buffer has a buffer strength between about 0.1 millimolar and about 1 Molar, and in other embodiments the concentration is between about 1 millimolar and about 900 millimolar, preferably between about 5 millimolar and about 800 millimolar and more preferably between about 10 millimolar and 700 millimolar.

In an embodiment, the present invention provides a stable oral solution comprising (a) clonidine HCl at a concentration of about 1 µg/mL or more; (b) pharmaceutically acceptable liquid vehicle; (c) at least one stabilizer; d) at least one buffer; and e) one or more other pharmaceutically acceptable excipients selected from pH adjusting agents, thickening agents, anti-oxidants, chelating agents, preservatives, flavoring agents, sweetening agents, coloring agents and mixtures thereof.

In an embodiment, the present invention provides a stable oral solution comprising (a) clonidine HCl at a concentration of about 10 µg/mL; (b) pharmaceutically acceptable liquid vehicle; (c) at least one stabilizer; d) at least one buffer; and e) one or more other pharmaceutically acceptable excipients selected from pH adjusting agents, thickening agents, anti-oxidants, chelating agents, preservatives, flavoring agents, sweetening agents, coloring agents and mixtures thereof.

In an embodiment, the present invention provides a stable oral solution comprising (a) clonidine HCl at a concentration of about 20 µg/mL; (b) pharmaceutically acceptable liquid vehicle; (c) at least one stabilizer; d) at least one buffer; and e) one or more other pharmaceutically acceptable excipients selected from pH adjusting agents, thickening agents, anti-oxidants, chelating agents, preservatives, flavoring agents, sweetening agents, coloring agents and mixtures thereof.

In certain embodiments, the pharmaceutical compositions of the present invention are buffer-free compositions. The term "buffer-free" or "free of buffer" in the context of this invention means that the present compositions and methods comprise no buffers.

In an embodiment, the present invention provides a stable oral solution comprising (a) clonidine HCl at a concentration of about 1 µg/mL or more; (b) pharmaceutically acceptable liquid vehicle; (c) at least one stabilizer; and d) one or more other pharmaceutically acceptable excipients selected from pH adjusting agents, thickening agents, anti-oxidants, chelating agents, preservatives, flavoring agents, sweetening agents, coloring agents and mixtures thereof, wherein said solution is substantially buffer-free.

In an embodiment, the present invention provides a stable buffer-free oral solution comprising (a) clonidine HCl at a concentration of about 1 µg/mL or more; (b) pharmaceutically acceptable liquid vehicle; (c) at least one stabilizer; and d) one or more other pharmaceutically acceptable excipients selected from pH adjusting agents, thickening agents, anti-oxidants, chelating agents, preservatives, flavoring agents, sweetening agents, coloring agents and mixtures thereof.

In an embodiment, the present invention provides a stable buffer-free oral solution comprising (a) clonidine HCl at a concentration of about 10 µg/mL; (b) pharmaceutically acceptable liquid vehicle; (c) at least one stabilizer; and d) one or more other pharmaceutically acceptable excipients selected from pH adjusting agents, thickening agents, anti-oxidants, chelating agents, preservatives, flavoring agents, sweetening agents, coloring agents and mixtures thereof.

In an embodiment, the present invention provides a stable buffer-free oral solution comprising (a) clonidine HCl at a concentration of about 20 µg/mL; (b) pharmaceutically acceptable liquid vehicle; (c) at least one stabilizer; and d) one or more other pharmaceutically acceptable excipients selected from pH adjusting agents, thickening agents, anti-oxidants, chelating agents, preservatives, flavoring agents, sweetening agents, coloring agents and mixtures thereof.

In an embodiment, the present invention provides a stable pharmaceutical solution for oral use comprising: (a) clonidine hydrochloride; (b) sodium chloride as stabilizer; (c) potassium sorbate as preservative; (d) purified water, wherein the solution is free of buffer.

Further, as used herein, the term "thickening agent" refers to agents that are generally used to thicken the liquid composition, which typically improves the mouth-feel of the composition, and/or to help coat the lining of the gastrointestinal tract. While any suitable thickening agent may be included in the compositions of the present invention, a preferred thickening agent, when used, includes one or more of acacia, alginic acid bentonite, carbomer, carboxymethylcellulose calcium or sodium, cetostearyl alcohol, methyl cellulose, ethylcellulose, gelatin guar gum, hydroxyethylcellulose (HEC), hydroxypropylcellulose (HPC), hydroxypropylmethylcellulose (HPMC), maltodextrin, polyvinyl alcohol, povidone, propylene carbonate, propylene glycol alginate, sodium alginate, sodium starch glycolate, starch tragacanth, and xanthan gum, and any combination thereof.

In an embodiment, the concentration of the stabilizer ranges from 0.001% to 20%, preferably 0.01% to 15.0%, more preferably 0.1% to 10.0%, based on total weight of the composition.

In an embodiment, the present invention provides a stable oral solution, wherein the solution comprises (a) clonidine HCl at a concentration of about 1 µg/mL or more; (b) pharmaceutically acceptable liquid vehicle; and (c) at least one stabilizer; and d) one or more other pharmaceutically acceptable excipients selected from pH adjusting agents, buffering agents, thickening agents, anti-oxidants, chelating agents, preservatives, flavoring agents, sweetening agents, coloring agents and mixtures thereof.

In an embodiment, the present invention provides a stable oral solution, wherein the solution comprises (a) clonidine HCl at a concentration of about 10 µg/mL; (b) pharmaceutically acceptable liquid vehicle; and (c) at least one stabilizer; and d) one or more other pharmaceutically acceptable excipients selected from pH adjusting agents, buffering agents, thickening agents, anti-oxidants, chelating agents, preservatives, flavoring agents, sweetening agents, coloring agents and mixtures thereof.

In an embodiment, the present invention provides stable oral solution, wherein the solution comprises (a) clonidine HCl at a concentration of about 20 µg/mL; (b) pharmaceutically acceptable liquid vehicle; and (c) at least one stabilizer; and d) one or more other pharmaceutically acceptable excipients selected from pH adjusting agents, buffering agents, thickening agents, anti-oxidants, chelating agents, preservatives, flavoring agents, sweetening agents, coloring agents and mixtures thereof.

In an embodiment, the present invention provides a stable oral solution, wherein the solution comprises (a) clonidine HCl; (b) pharmaceutically acceptable liquid vehicle; (c) at least one stabilizer; (d) at least one preservative; and one or more other pharmaceutically acceptable excipients selected from pH adjusting agents, buffering agents, thickening agents, anti-oxidants, chelating agents, flavoring agents, sweetening agents, coloring agents and mixtures thereof.

In an embodiment, the present invention provides a stable oral solution, wherein the solution comprises (a) clonidine HCl; (b) pharmaceutically acceptable liquid vehicle; (c) at least one stabilizer; (d) at least one preservative; and (e) one or more other pharmaceutically acceptable excipients selected from pH adjusting agents, buffering agents, thickening agents, anti-oxidants, chelating agents, flavoring agents, sweetening agents, coloring agents and mixtures thereof, wherein the solution has a pH in the range of about 3 to about 9, preferably between about 4 to about 8.

In an embodiment, the present invention provides a stable oral solution, wherein the solution comprises (a) clonidine HCl; (b) purified water; (c) at least one stabilizer; and d) one or more other pharmaceutically acceptable excipients selected from pH adjusting agents, buffering agents, thickening agents, anti-oxidants, chelating agents, preservatives, flavoring agents, sweetening agents, coloring agents and mixtures thereof.

In an embodiment, the present invention provides a stable oral solution, wherein the solution comprises (a) clonidine HCl; (b) purified water; (c) sodium chloride; and d) one or more other pharmaceutically acceptable excipients selected from pH adjusting agents, buffering agents, thickening agents, anti-oxidants, chelating agents, preservatives, flavoring agents, sweetening agents, coloring agents and mixtures thereof.

In an embodiment, the present invention provides a stable oral solution, wherein the solution comprises (a) clonidine HCl; (b) purified water; (c) sodium chloride; (d) potassium sorbate; and (e) one or more other pharmaceutically acceptable excipients selected from pH adjusting agents, buffering agents, thickening agents, anti-oxidants, chelating agents, flavoring agents, sweetening agents, coloring agents and mixtures thereof.

In an embodiment, the present invention provides a stable oral solution, wherein the solution comprises (a) clonidine HCl; (b) purified water; (c) sodium chloride; (d) sodium propionate; and (e) one or more other pharmaceutically acceptable excipients selected from pH adjusting agents, buffering agents, thickening agents, anti-oxidants, chelating agents, flavoring agents, sweetening agents, coloring agents and mixtures thereof.

In an embodiment, the present invention provides a stable aqueous oral solution comprising: (a) clonidine hydrochloride; (b) sodium chloride; (c) potassium sorbate; (d) purified water, wherein the solution is free of buffer, wherein the solution is free of paraben, wherein solution exhibits in-use shelf life for at least one month when stored at room temperature.

In an embodiment, the present invention provides a stable aqueous oral solution comprising: (a) about 20 µg/mL of clonidine hydrochloride; (b) about 0.25% w/w of sodium chloride; (c) about 0.1% w/w potassium sorbate; (d) purified water, wherein the solution is free of buffer, wherein the solution is free of paraben, wherein solution exhibits in-use shelf life for at least one month when stored at room temperature.

In another embodiment, the present invention provides a process for preparing a stable, liquid pharmaceutical formulation for oral administration, wherein the process comprises:
 (a) adding at least one stabilizer and at least one sweetener to one or more pharmaceutically acceptable solvents under continuous stirring at room temperature to form a clear solution;
 (b) optionally adding at least one preservative to the above solution under continuous stirring at room temperature to form a clear solution;
 (c) adding at least one flavoring agent to the above solution under continuous stirring at room temperature to form a clear solution;
 (d) adjusting the pH of the solution with one or more pH adjusting agents in the pH range of 4-8;
 (e) adding clonidine hydrochloride to the above solution under constant stirring at room temperature to obtain clear solution;
 (f) making up the final volume with one or more pharmaceutically acceptable solvents and stirring to obtain a final clear solution;
 (g) filling the bulk solution into suitable container followed by closing with a cap and sealing.

The pharmaceutical compositions of present application may be filled into any suitable pharmaceutically acceptable containers. For example, the pharmaceutically acceptable container may be selected from group consisting of bottles and syringes.

The bottle as used herein is made of any material convenient with the storage and the use requirements comprising polymers, metal and glass and so on. It is of importance that the bottle material does not interfere with the components of the liquid formulation as disclosed herein. In an embodiment, the bottle is made of glass. In order to protect the active ingredient from light-induced degradation, the bottle is preferably an amber glass bottle.

The bottle capacity can be adapted to the volume to be administrated for the period during which the liquid formulation as disclosed herein is stable. For instance, a solution which is stable for 10 days after opening associated to an administration of dose up to 0.6 mg of clonidine per day may be stored into bottle of about 200 mL. The one skilled in the art will easily adapt the volume of the bottle to that needed as previously suggested.

A pipette as used herein is made of glass, plastic or any material convenient for the use and storage of the liquid solutions as disclosed herein. The pipette may be graduated to facilitate the administration of the liquid solution. In a more specific embodiment of the present disclosure, the pipette is a 1 mL graduated pipette.

A cap (or closure) as used herein is any article for closing a suitably shaped opening. Said cap encompasses, but is not limited to, childproof closures, waterproof closures, pipette associated caps, solid caps, plastic or polymeric caps. In an embodiment, the cap is screwed on the bottle top or interlocked with the top of the bottle.

A sealing element may be required to maintain tightness of the system, wherein said element may be a bottle-cap, bottle-pipette-cap, bottle-pipette or pipette-cap. This element can be supplied on its own and further fit in the bottle-neck, or around the pipette, or in the cap, or it can be pre-adapted to the bottle, the cap or the pipette.

In a certain aspect, the invention relates to a kit of parts comprising a package containing one or more bottles of the liquid formulation as disclosed herein and one or more pipettes intended to remove the needed amount of the liquid formulation, and/or instructions.

In another aspect, the invention relates to a kit comprising parts allowing the extemporaneous preparation of the solutions according to the invention.

In an embodiment, the pharmaceutically acceptable container may be a bottle, wherein the bottle is selected from group consisting of a glass bottle and a plastic bottle. Examples of glass bottle include, but are not limited to Type 1, ∥ and Ill borosilicate glass bottles. In an embodiment, the pharmaceutically acceptable container is a glass bottle, wherein the glass bottle may be amber color glass bottle or clear glass bottle. In a preferred embodiment, the bottles will be available in 30, 60, 100, 120, 150, 200, 250 and 500 mL fill volumes. Examples of plastic bottles include, but are not limited to, high density polyethylene (HDPE), low density polyethylene (LDPE), PET (Polyethylene Terephthalate) and polypropylene (PP) bottles. In certain embodiments of the invention, the pharmaceutically acceptable container is a plastic bottle, wherein the plastic bottle may be amber color, white opaque or translucent plastic bottle. In preferred embodiment, the pharmaceutically acceptable container is a HDPE bottle in 30, 60, 115, 120, 200, 250 & 500 mL fill volumes.

In an embodiment, the pharmaceutical composition of the present disclosure is packed in a kit comprising a bottle with child resistant cap, dosing syringe, adapter and dosing syringe.

In an embodiment, the pharmaceutical composition of the present disclosure having extended stability, comprising (i) clonidine hydrochloride at a concentration of about 20 µg/mL; (ii) at least one pharmaceutically acceptable vehicle; (iii) at least one stabilizer; and (iv) at least one preservative; wherein said composition is provided in a polyethylene terephthalate (PET) bottle.

In an embodiment, the pharmaceutical composition of the present disclosure having extended stability, comprising (i) clonidine hydrochloride at a concentration of about 20 µg/mL; (ii) at least one pharmaceutically acceptable vehicle; (iii) at least one stabilizer; and (iv) at least one preservative; wherein said composition is provided in a high-density polyethylene (HDPE) bottle.

In an embodiment, the pharmaceutical composition of the present disclosure having extended stability, comprising (i) clonidine hydrochloride at a concentration of about 20 µg/mL; (ii) at least one pharmaceutically acceptable vehicle; (iii) at least one stabilizer; and (iv) at least one preservative; wherein said composition is provided in a glass bottle Stability: As used herein, the term "stable" or "extended stability" is defined as no more than about 10% loss of clonidine under typical commercial storage conditions. In certain embodiments, the compositions of the present invention will have no more than about 5% loss of clonidine, more preferably, no more than about 2% loss of clonidine, under typical commercial storage conditions. The composition retains at least about 90% of the potency of clonidine after storing the composition at 40° C./75% RH or 40° C./25% RH or 30° C./25% RH or 25° C./60% RH or 25° C./40% RH for at least 3 months, at least 6 months, at least 9 months, at least 12 months, at least 15 months, at least 18 months, at least 21 months, at least 24 months, at least 30 months and at least 36 months. In certain aspects, the term "stable" or "extended stability" refers to chemical stability, wherein not more than 2% w/w of total impurities, preferably not more than 1.5% w/w of total impurities, more preferably not more than 1% w/w of total impurities are formed on storage at accelerated conditions of stability at 40° C./75% RH, 40° C./25% RH, 30° C./25% RH, 25° C./60% RH or 25° C./40% RH for at least 3 months, at least 6 months, at least 9 months, at least 12 months, at least 15 months, at least 18 months, at least 21 months, at least 24 months, at least 30 months and at least 36 months.

In an embodiment, the pharmaceutical composition of the present disclosure having extended stability, comprises (i) clonidine hydrochloride at a concentration of about 20 µg/mL; (ii) at least one pharmaceutically acceptable vehicle; (iii) at least one stabilizer; and (iv) at least one preservative; wherein said composition is stable for at least 3 months, at least 6 months, at least 9 months, at least 12 months, at least 15 months, at least 18 months, at least 21 months, at least 24 months, at least 30 months and at least 36 months when stored at 25° C./60% RH or 25° C./40% RH.

In an embodiment, the present invention provides a stable oral solution comprising (i) clonidine HCl; (ii) at least one pharmaceutically acceptable liquid vehicle; (iii) one or more stabilizers; and (iv) one or more pharmaceutically acceptable excipients selected from pH adjusting agents, buffering agents, thickening agents, anti-oxidants, chelating agents, preservatives, flavoring agents, sweetening agents, coloring agents and mixtures thereof, wherein the solution is stable for at least 6 months at 40° C./75% RH or 40° C./25% RH or 30° C./25% RH or 25° C./60% RH or 25° C./40% RH condition.

In an embodiment, the present invention provides a stable liquid pharmaceutical composition suitable for oral administration comprising: (i) clonidine or its pharmaceutically acceptable salt at a concentration of about 20 µg/mL; (ii) at least one pharmaceutically acceptable vehicle; and (iii) at least one pharmaceutically acceptable excipient, wherein said composition is stable for at least 6 months when stored at 25° C./60% RH.

In particular, clonidine USP related Compound A, 2,6-Dichloroanline impurity, N-(2,6-Dichlorophenyl) formamide impurity, 2,6-Dichloroacetanilide impurity, (2,6-Dichlorophenyl) carbonimidicdichloride impurity and 4-hydroxy clonidine impurity were monitored known impurities. The structures of these impurities are shown below:

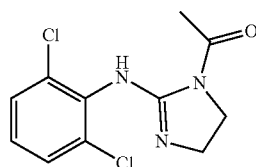
Clonidine USP related Compound A

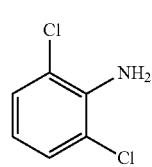
2,6-Dichloroaniline Impurity

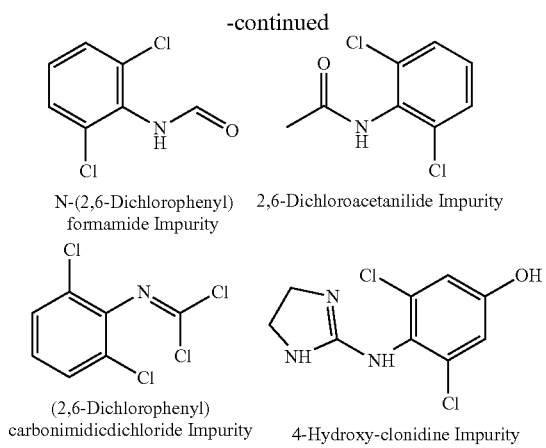

N-(2,6-Dichlorophenyl) formamide Impurity 2,6-Dichloroacetanilide Impurity (2,6-Dichlorophenyl) carbonimidicdichloride Impurity 4-Hydroxy-clonidine Impurity In an embodiment, the present invention provides a stable oral solution comprising (a) clonidine HCl; (b) pharmaceutically acceptable liquid vehicle; (c) at least one stabilizer; and (d) one or more other pharmaceutically acceptable excipients, wherein the level of total impurities in the composition is less than about 10% w/w, preferably less than about 5.0% w/w, preferably less than about 2.5% w/w, more preferably less than about 1.5% w/w, more preferably less than about 0.5% w/w as measured by HPLC.

In another embodiment, the level of any unknown impurity in the inventive pharmaceutical composition resulting from the degradation of clonidine is less than about 5% (w/w), preferably less than about 4% (w/w), preferably less than about 3% (w/w), preferably less than about 2% (w/w), preferably less than about 1% (w/w), preferably less than about 0.8% (w/w), preferably less than about 0.5% (w/w), preferably less than about 0.25% (w/w), preferably less than about 0.15% (w/w) and more preferably less than about 0.1% (w/w) as measured by HPLC.

In yet another embodiment, the level of clonidine USP related Compound A impurity or 2,6-Dichloroanline impurity or N-(2,6-Dichlorophenyl) formamide impurity or 2,6-Dichloroacetanilide impurity or (2,6-Dichlorophenyl) carbonimidicdichloride impurity or 4-hydroxy clonidine impurity or any other known impurity in the inventive pharmaceutical composition resulting from the degradation of clonidine is less than about 5% (w/w), preferably less than about 4% (w/w), preferably less than about 3% (w/w), preferably less than about 2% (w/w), preferably less than about 1% (w/w), preferably less than about 0.5% (w/w), preferably less than about 0.25% (w/w), preferably less than about 0.15% (w/w) and more preferably less than about 0.1% (w/w) as measured by HPLC.

Dosage and Administration: In another embodiment, the invention includes methods of using stable, liquid pharmaceutical compositions of clonidine in treating essential and secondary hypertension. In an embodiment, a method of treating essential and secondary hypertension using stable liquid pharmaceutical compositions of clonidine, comprises orally administering to a subject about 1 µg/mL to about 500 µg/mL of clonidine, wherein the pharmaceutical composition further comprises at least one pharmaceutically acceptable liquid vehicle, stabilizer and at least one other pharmaceutically acceptable excipient.

In yet another embodiment, the invention includes methods of using stable, liquid pharmaceutical compositions of clonidine in treating or preventing hypertension, neonatal abstinence syndrome (NAS), tourette's syndrome, migraine, headaches, recurrent vascular headaches, attention deficit hyperactivity disorder (ADHD) and vasomotor conditions associated with menopause and characterized by flushing. The therapeutic doses most commonly employed have ranged from 0.2 mg to 0.6 mg given in divided doses (not exceeding 2.4 mg/day).

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the disease progression is slowed or lengthened as compared to the extent or time course in the absence of treatment.

In one embodiment, the dose of clonidine is in the range of from about 0.1 µg/kg/day to about 100 µg/kg/day.

In one embodiment, the dose of clonidine administered to adult or pediatric patients is 0.1 µg/kg/day, 0.2 µg/kg/day, 0.3 µg/kg/day, 0.4 µg/kg/day, 0.5 µg/kg/day, 0.6 µg/kg/day, 0.7 µg/kg/day, 0.8 µg/kg/day, 0.9 µg/kg/day, 1 µg/kg/day, 1.1 µg/kg/day, 1.2 µg/kg/day, 1.3 µg/kg/day, 1.4 µg/kg/day, 1.5 µg/kg/day, 1.6 µg/kg/day, 1.7 µg/kg/day, 1.8 µg/kg/day, 1.9 µg/kg/day, 2 µg/kg/day, 2.1 µg/kg/day, 2.2 µg/kg/day, 2.3 µg/kg/day, 2.4 µg/kg/day, 2.5 µg/kg/day, 2.6 µg/kg/day, 2.7 µg/kg/day, 2.8 µg/kg/day, 2.9 µg/kg/day, 3 µg/kg/day, 3.1 µg/kg/day, 3.2 µg/kg/day, 3.3 µg/kg/day, 3.4 µg/kg/day, 3.5 µg/kg/day, 3.6 µg/kg/day, 3.7 µg/kg/day, 3.8 µg/kg/day, 3.9 µg/kg/day, 4 µg/kg/day, 4.1 µg/kg/day, 4.2 µg/kg/day, 4.3 µg/kg/day, 4.4 µg/kg/day, 4.5 µg/kg/day, 4.6 µg/kg/day, 4.7 µg/kg/day, 4.8 µg/kg/day, 4.9 µg/kg/day, 5 µg/kg/day, 5.1 µg/kg/day, 5.2 µg/kg/day, 5.3 µg/kg/day, 5.4 µg/kg/day, 5.5 µg/kg/day, 5.6 µg/kg/day, 5.7 µg/kg/day, 5.8 µg/kg/day, 5.9 µg/kg/day, 6 µg/kg/day, 6.1 µg/kg/day, 6.2 µg/kg/day, 6.3 µg/kg/day, 6.4 µg/kg/day, 6.5 µg/kg/day, 6.6 µg/kg/day, 6.7 µg/kg/day, 6.8 µg/kg/day, 6.9 µg/kg/day, 7 µg/kg/day, 7.1 µg/kg/day, 7.2 µg/kg/day, 7.3 µg/kg/day, 7.4 µg/kg/day, 7.5 µg/kg/day, 7.6 µg/kg/day, 7.7 µg/kg/day, 7.8 µg/kg/day, 7.9 µg/kg/day, 8 µg/kg/day, 8.1 µg/kg/day, 8.2 µg/kg/day, 8.3 µg/kg/day, 8.4 µg/kg/day, 8.5 µg/kg/day, 8.6 µg/kg/day, 8.7 µg/kg/day, 8.8 µg/kg/day, 8.9 µg/kg/day, 9 µg/kg/day, 9.1 µg/kg/day, 9.2 µg/kg/day, 9.3 µg/kg/day, 9.4 µg/kg/day, 9.5 µg/kg/day, 9.6 µg/kg/day, 9.7 µg/kg/day, 9.8 µg/kg/day, 9.9 µg/kg/day, 10 µg/kg/day, 11 µg/kg/day, 12 µg/kg/day, 13 µg/kg/day, 14 µg/kg/day, 15 µg/kg/day, 16 µg/kg/day, 17 µg/kg/day, 18 µg/kg/day, 19 µg/kg/day, 20 µg/kg/day, 30 µg/kg/day, 40 µg/kg/day, 50 µg/kg/day, 60 µg/kg/day, 70 µg/kg/day, 80 µg/kg/day, 90 µg/kg/day, 100 µg/kg/day, In some embodiment, the above-described dose of clonidine can be administered as a single dose or divided dose over a period of 2-10 days.

The dosage levels are dependent on the nature of the condition, drug efficacy, condition of the patient, judgment of the practitioner, frequency and mode of administration. The unit dosage forms can be administered to achieve any daily amount described herein, such as by administering one to five times daily (e.g., one, two, three, four, or five times daily).

General HPLC procedure: As explained in detail below, the following HPLC procedure can be used to detect, quantify impurities of clonidine hydrochloride and to determine assay % of clonidine hydrochloride & preservatives. The materials and general conditions are listed below:

TABLE 1

Assay of Clonidine HCl identification by HPLC chromatographic conditions

| | |
|---|---|
| Chromatographic Mode | HPLC system equipped with UV/PDA detector |
| Column | C18, 4.6 × 150 mm, 5 μm |
| Wavelength | 220 nm |
| Flow rate | 1.0 mL/minute |
| Injection volume | 20 μL |
| Column temperature | 35° C. |
| Temperature Sample temperature | 25° C. |
| Run time | 45 minutes |
| Mobile Phase A | transfer 1.0 mL of Triethylamine into 1000 ml of water, mix well and adjust the pH of the solution to 6.90 ± 0.05 using dilute orthophosphoric acid solution. |
| Mobile Phase B | Filter water through a 0.45μ membrane filter. Mix 400 mL of water and 600 mL of Acetonitrile, transfer 1.0 ml of Triethylamine to it and adjust the pH of the solution to 6.90 ± 0.05 using dilute orthophosphoric acid solution. |
| Mode of Elution | Gradient |

| Time | Mobile Phase-A (%) | Mobile Phase B (%) |
|---|---|---|
| 0 | 95 | 5 |
| 15 | 95 | 5 |
| 25 | 90 | 10 |
| 28 | 90 | 10 |
| 29 | 20 | 80 |
| 35 | 20 | 80 |
| 36 | 95 | 5 |
| 45 | 95 | 5 |

TABLE 2

Related substances identification by HPLC Chromatographic conditions

| | |
|---|---|
| Chromatographic Mode | HPLC system equipped with UV/PDA detector |
| Column | C18, 4.6 × 150 mm, 3.5 μm |
| Wavelength | 210 nm |
| Flow rate | 0.8 mL/minute |
| Injection volume | 100 μL |
| Column temperature | 30° C. |
| Temperature Sample temperature | 25° C. |
| Run time | 65 minutes |
| Mobile Phase A | Buffer (pH 6.5, 20 mM phosphate buffer with 0.2% of 1-decane sulfonic acid sodium salt as an ion pair) solution and acetonitrile in the ratio of 90:10 (% v/v). |
| Mobile Phase B | Buffer (pH 6.5, 20 mM phosphate buffer with 0.2% of 1-decane sulfonic acid sodium salt as an ion pair) solution and acetonitrile in the ratio of 50:50 (% v/v). |
| Mode of Elution | Gradient |

| Time | Mobile Phase-A (%) | Mobile Phase B (%) |
|---|---|---|
| 0 | 100 | 0 |
| 10 | 80 | 20 |
| 40 | 40 | 60 |
| 50 | 40 | 60 |
| 51 | 0 | 100 |
| 55 | 0 | 100 |
| 56 | 100 | 0 |
| 65 | 100 | 0 |

TABLE 3

Assay of potassium sorbate preservative identification by HPLC chromatographic conditions

| | |
|---|---|
| Chromatographic Mode | HPLC system equipped with UV/PDA detector |
| Column | C18, 4.6 × 150 mm, 3.5 μm |
| Wavelength | 264 nm |
| Flow rate | 1.0 mL/minute |
| Injection volume | 10 μL |
| Column temperature | 40° C. |
| Temperature Sample temperature | 25° C. |
| Run time | 30 minutes |
| Mobile Phase A | transfer 1.0 mL of Trifluoroacetic acid into 1000 ml of water, and mix well. |
| Mobile Phase B | transfer 1.0 mL of Trifluoroacetic acid into 1000 ml of methanol, and mix well. |
| Mode of Elution | Gradient |

| Time | Mobile Phase-A (%) | Mobile Phase B (%) |
|---|---|---|
| 0.0 | 75 | 25 |
| 17.0 | 75 | 25 |
| 18.0 | 5 | 95 |
| 23.0 | 5 | 95 |
| 23.1 | 75 | 25 |
| 30.0 | 75 | 25 |

TABLE 4

Assay of sodium propionate preservative identification by HPLC chromatographic conditions

| | |
|---|---|
| Chromatographic Mode | HPLC system equipped with UV/PDA detector |
| Column | C18, 4.6 × 250 mm, 3 μm |
| Wavelength | 210 nm |
| Flow rate | 1.0 mL/minute |
| Injection volume | 20 μL |
| Column temperature | 30° C. |
| Temperature Sample temperature | 25° C. |
| Run time | 30 minutes |
| Mobile Phase A | transfer 1.0 mL of orthophosphoric acid into 1000 mL of water: methanol 90:10 composite solution, and mix well. |
| Mobile Phase B | transfer 1.0 mL of orthophosphoric acid into 1000 ml of water: methanol 10:90 composite solution, and mix well. |
| Mode of Elution | Gradient |

| Time | Mobile Phase-A (%) | Mobile Phase B (%) |
|---|---|---|
| 0.0 | 100 | 0 |
| 14.0 | 100 | 0 |
| 15.0 | 0 | 100 |
| 20.0 | 0 | 100 |
| 21.0 | 100 | 0 |
| 30.0 | 100 | 0 |

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

Example 1

Clonidine compositions are set forth in Table 5 below:

TABLE 5

| Composition Ingredients | 001 | 002 | 003 | 004 | 005 | 006 | 007 |
|---|---|---|---|---|---|---|---|
| | | | | Quantity (mg/mL) | | | |
| Clonidine HCl | 0.02 | 0.02 | 0.02 | 0.02 | 0.02 | 0.02 | 0.02 |
| Potassium sorbate | 1.80 | 1.80 | 1.80 | 1.80 | 1.80 | 0.9 | 1.80 |
| L-Histidine | 0.500 | — | — | — | — | — | — |
| Meglumine | — | 0.056 | — | — | — | — | — |
| L-arginine | — | — | 0.025 | — | — | — | — |
| Tromethamine | — | — | — | 0.050 | — | — | — |
| Sodium chloride | — | — | — | — | 5.84 | 2.92 | — |
| Sucralose | 0.40 | 0.40 | 0.40 | 0.40 | 0.40 | 0.20 | 0.40 |
| Mixed berry flavor | 2.00 | 2.0 | 2.0 | 2.0 | 2.0 | 1.0 | 2.0 |
| 0.1N HCl | pH not adjusted | | | q.s. to adjust pH to 5-6 | | | |
| Purified water | | | | q.s | | | |

Manufacturing Procedure of Compositions 001-007:

Stabilizer or sweetener was added to a small portion of purified water and stirred continuously at room temperature to get a clear solution. Preservative (potassium sorbate) was added to the above solution and mixed to get a clear solution. Next, flavoring agent was added to the above solution and stirred continuously at room temperature to get a clear solution. pH of the above solution was adjusted using 0.1 N HCl to a pH in the range of 5 to 6. Clonidine was added to the resulting solution under continuous stirring at room temperature to get a clear solution. Purified water was added to make up the final volume. pH of the solution was checked to ensure it is be between 5.0 to 6.0.

TABLE 6

Analytical data for composition 001

| | Initial at | Storage condition | |
|---|---|---|---|
| | | 40° C./75% RH | 25° C./60% RH |
| | | Storage duration (in months) | |
| | RT | 3 | 3 |
| Storage container Description | Clear | HDPE Bottle Clear yellow color | Clear |
| pH | 7.60 | 7.63 | 7.86 |
| Assay-Clonidine HCl (%) | 100.4 | 92.3 | 99.6 |
| Assay-Preservative content (%) | 94.7 | 90.2 | 93 |
| Related substance | | % Impurity | |
| 4-Hydroxy clonidine Imp. | ND | ND | ND |
| Single max. unknown Imp. | 0.112 | 0.96 | 0.05 |
| Total Impurities | 0.11 | 2.62 | 0.05 |

RT = Room Temperature;
3M = 3 months

TABLE 7

Analytical data for composition 002

| | Initial | Test | | | |
|---|---|---|---|---|---|
| | | 40° C./75% RH | | 25° C./60% RH | |
| | | Storage duration (in months) | | | |
| | @ RT | 1 | 1 | 1 | 1 |
| Storage Container | | PET Bottle | HDPE Bottle | PET Bottle | HDPE Bottle |
| Description | Clear | Clear | Clear | Clear | Clear |
| pH | 5.68 | 5.68 | 5.71 | 5.58 | 5.72 |

TABLE 7-continued

Analytical data for composition 002

| | Initial | Test | | | |
|---|---|---|---|---|---|
| | | 40° C./75% RH | | 25° C./60% RH | |
| | | Storage duration (in months) | | | |
| | @ RT | 1 | 1 | 1 | 1 |
| Assay-Clonidine HCl (%) | 97.9 | 96.3 | 96.9 | 97.6 | 96.4 |
| Assay-Preservative content (%) | 95.9 | 96.0 | 96.2 | 96.8 | 97.0 |
| Related substance | | % Impurity | | | |
| 4-Hydroxy clonidine Imp. | ND | ND | ND | ND | ND |
| Single max. unknown Imp. | ND | 0.18 | 0.2 | 0.03 | 0.37 |
| Total Impurities | ND | 0.34 | 0.36 | 0.03 | 0.59 |

TABLE 8

Analytical data for composition 003

| | Initial | Test | | | |
|---|---|---|---|---|---|
| | | 40° C./75% RH | | 25° C./60% RH | |
| | | Storage duration (in months) | | | |
| | @RT | 1 | 1 | 1 | 1 |
| Storage Container | | PET Bottle | HDPE Bottle | PET Bottle | HDPE Bottle |
| Description | Clear | Clear | Clear | Clear | Clear |
| pH | 5.75 | 5.79 | 5.78 | 5.74 | 5.72 |

TABLE 8-continued

Analytical data for composition 003

|  | Initial | Test 40° C./75% RH | | 25° C./60% RH | |
|---|---|---|---|---|---|
|  |  | Storage duration (in months) | | | |
|  | @RT | 1 | 1 | 1 | 1 |
| Assay-Clonidine HCl (%) | 99.9 | 98.8 | 96.6 | 99.8 | 99.5 |
| Assay-Preservative content (%) | 96.8 | 96.4 | 96.3 | 97.2 | 97.6 |
| Related substance | | % Impurity | | | |
| 4-Hydroxy clonidine Imp. | ND | ND | ND | ND | ND |
| Single max. unknown Imp. | ND | 0.17 | 0.35 | 0.43 | 0.34 |
| Total Impurities | ND | 0.5 | 0.88 | 0.5 | 0.69 |

TABLE 9

Analytical data for composition 004

|  | Initial | Test 40° C./75% RH | | 25° C./60% RH | |
|---|---|---|---|---|---|
|  |  | Storage duration (in months) | | | |
|  | @ RT | 1 | 1 | 1 | 1 |
| Storage Container |  | PET Bottle | HDPE Bottle | PET Bottle | HDPE Bottle |
| Description | Clear | Clear | Clear | Clear | Clear |
| pH | 5.68 | 5.68 | 5.70 | 5.55 | 5.66 |
| Assay-Clonidine HCl (%) | 96.0 | 97.8 | 96.5 | 98.5 | 99.7 |
| Assay-Preservative content (%) | 98.3 | 97.5 | 97.5 | 98.8 | 98.2 |
| Related substance | | % Impurity | | | |
| 4-Hydroxy clonidine Imp. | ND | ND | ND | ND | ND |
| Single max. unknown Imp. | 0.612 | 0.08 | 0.04 | 0.29 | 0.21 |
| Total Impurities | 0.612 | 0.24 | 0.1 | 0.48 | 0.25 |

TABLE 10

Analytical data for composition 005
Composition 005

|  | Storage condition Room temperature | | |
|---|---|---|---|
|  |  | 40° C./ 75% RH | 40° C./ 75% RH |
|  |  | Storage duration | |
|  | Initial | 1 month | 2 months |
| Storage container |  | HDPE Bottle | |
| Description | Clear | Clear | Clear |
| pH | 5.48 | 5.46 | 5.47 |
| Assay-Clonidine HCl (%) | 98.7 | 96.5 | 96.7 |
| Assay-Preservative content (%) | 97.6 | 97.3 | 98.2 |
| Related substance |  | % Impurity |  |
| 4-Hydroxy clonidine Impurity | ND | ND | ND |
| Single max. unknown Imp. | 0 | 0.06 | 0.09 |
| Total Impurities | 0 | 0.06 | 0.24 |

Composition 005 was physically and chemically stable for at least 2 months, without visible particles and with no significant change in assay at 4000/75% RH. Impurity profile was also found to be satisfactory.

TABLE 11

Analytical data for composition 006
Composition 006

|  | Storage condition Room temperature | | |
|---|---|---|---|
|  |  | 40° C./ 75% RH | 40° C./ 75% RH |
|  |  | Storage duration (in months) | |
|  | Initial | 1 | 2 |
| Storage container |  | HDPE Bottle | |
| Description | Clear | Clear | Clear |
| pH | 5.51 | 5.47 | 5.54 |
| Assay-Clonidine HCl (%) | 96.4 | 96.4 | 96.1 |
| Assay-Preservative content (%) | 98.0 | 98.3 | 98.0 |
| Related substance |  | % Impurity |  |
| 4-Hydroxy clonidine Impurity | ND | ND | ND |
| Single max. unknown Imp. | ND | ND | 0.03 |
| Total Impurities | ND | ND | 0.06 |

Composition 006, was physically and chemically stable for at least 1 month, without visible particles and with no significant change in assay at 40° C./75% RH condition. Impurity profile was also found to be satisfactory.

TABLE 12

Analytical data for composition 007
Composition 007

| Storage condition | RT | 40° C./75% RH | | | 25° C./60% RH | | |
|---|---|---|---|---|---|---|---|
| Storage container | — | PET | HDPE | Glass | PET | HDPE | Glass |
| Storage duration | Initial | 1 month | | | | | |
| Description | Clear | Clear | | | | | |
| pH | 5.63 | 5.71 | 5.71 | 5.74 | 5.71 | 5.70 | 5.61 |
| Assay-Clonidine HCl (%) | 94.9 | 86.1 | 86.4 | 94.5 | 87.4 | 86.9 | 94.8 |

TABLE 12-continued

Analytical data for composition 007

| | | Composition 007 | | | | | |
|---|---|---|---|---|---|---|---|
| Storage condition | RT | 40° C./75% RH | | | 25° C./60% RH | | |
| Storage container | — | PET | HDPE | Glass | PET | HDPE | Glass |
| Assay-Preservative content (%) | 97.8 | 96.7 | 96.8 | 97.8 | 97.6 | 97.7 | 98.6 |
| Related substance | | | | % Impurity | | | |
| 4-Hydroxy-clonidine Imp | ND | ND | ND | ND | ND | ND | ND |
| Single max. unknown Imp. | ND | 0.59 | 0.58 | 0.11 | 0.56 | 0.73 | 0.36 |
| Total Impurities | ND | 1.04 | 1.00 | 0.21 | 0.72 | 1.38 | 0.4 |

*RT = Room temperature;
PET = Polyethylene Terephthalate;
HDPE = High Density Polyethylene In amber color glass bottles, Composition 007 was physically and chemically stable for at least 1 month, without visible particles and with no significant change in assay. Clonidine remains solubilized and compositions were found to be clear without any recrystallization or precipitation. However, in HDPE and PET bottles there was a significant rise in impurity profile.

Example 2

Clonidine compositions are set forth in Table 13 below:

TABLE 13

| Ingredients | Composition 008 |
|---|---|
| Clonidine HCl | 0.02 |
| Potassium sorbate | — |
| Sodium propionate | 0.6 |
| Sucralose | 0.2 |
| Mixed berry flavor | 0.2 |
| 0.1N HCl | q.s. to adjust pH 5.0 to 6.0 |
| Purified water | q.s. |

Manufacturing Procedure of Compositions 008:

Sucralose was added to a small portion of purified water and stirred continuously at room temperature to get a clear solution. Sodium propionate was added to the above solution and mixed to get a clear solution. Next, the flavoring agent was added to the above solution and stirred continuously at room temperature to get a clear solution. pH of the above solution was adjusted using 0.1 N HCl to a pH in the range of 5 to 6. Clonidine was added to the resulting solution under continuous stirring at room temperature to get a clear solution. Purified water was added to make up the final volume. pH of the solution was checked to ensure it is between 5.0 to 6.0.

Example 3

Clonidine compositions are set forth in Table 14 below:

TABLE 14

| Ingredients | Composition 009 Quantity (mg/mL) |
|---|---|
| Clonidine HCl | 0.02 |
| Sodium chloride | 2.50 |
| Sucralose | 0.20 |

TABLE 14-continued

| Ingredients | Composition 009 Quantity (mg/mL) |
|---|---|
| Mixed berry flavor | 0.20 |
| 0.5N HCl | q.s. to adjust pH to 5-6 |
| Purified water | q.s. |

Manufacturing Procedure of Composition 009:

Sodium chloride and sucralose were added to small portion of purified water and stirred continuously at room temperature to get a clear solution. Next, flavoring agent was added to above solution and stirred continuously at room temperature to get a clear solution. pH of the above solution was adjusted using 0.5 N HCl to a pH in the range of 5 to 6. Clonidine was added to the resulting solution under continuous stirring at room temperature to get a clear solution. Purified water was added to make up the final volume. pH of the solution was checked to ensure it is between 5.0 to 6.0.

Example 4

Clonidine compositions are set forth in Table 15 below.

TABLE 15

| | Composition | | | | |
|---|---|---|---|---|---|
| | 010 | 011 | 012 | 013 | 023 |
| Ingredients | Quantity (mg/mL) | | | | |
| Clonidine HCl | 0.02 | 0.02 | 0.02 | 0.02 | 0.02 |
| Sodium chloride | 2.50 | 2.50 | 2.5 | 2.5 | 2.50 |
| Potassium sorbate | 1.0 | 1.0 | — | — | 1.0 |
| Sodium propionate | — | — | 0.6 | 0.6 | — |
| Sucralose | 0.20 | 0.20 | 0.20 | 0.20 | 0.20 |
| Mixed berry flavor | 0.20 | 0.20 | 0.20 | 0.20 | 0.20 |
| 0.1N HCl | q.s. to adjust pH to 5-6 | q.s. to adjust pH to 4-5 | q.s. to adjust pH to 5-6 | q.s. to adjust pH to 4-5 | No pH adjustment |
| Purified water | q.s. | q.s. | q.s. | q.s. | q.s. |

Manufacturing Procedure of Compositions 010 to 013 and 023:

Sodium chloride and sucralose were added to a small portion of purified water and stirred continuously at room temperature to get a clear solution. Potassium sorbate/sodium propionate was added to the above solution and mixed to get a clear solution. Next, the flavoring agent was added to the above solution and stirred continuously at room temperature to get a clear solution. The pH of the above solution was adjusted using 0.1N HCl (except for composition 023). Clonidine Hydrochloride was added to the above resulting solution under continuous stirring at room temperature to get a clear solution. Purified water was added to make up the final volume. pH of the solution was checked to ensure it is between the desired range.

TABLE 16

| Composition 010 | | | |
|---|---|---|---|
| Storage container | Amber bottle | | |
| | Storage condition | | |
| | 40° C./75% RH | | 25° C./60% RH |
| | Storage duration (in months) | | |
| | Initial | 6 | 6 |
| Description | A Clear colorless solution | | |
| pH | 5.51 | 5.63 | 5.58 |
| Assay of Clonidine HCl (%) | 96.2 | 93.7 | 97.7 |
| Assay of Preservative | 101.2 | 99.3 | 100.1 |
| 4-Hydroxy Clonidine Impurity | ND | <LOQ | ND |
| Any unspecified degradation Product | ND | 0.35 | <LOQ |
| Total Impurities | ND | 0.56% | <LOQ |

LOQ = Limit of Quantification

TABLE 17

| Composition 011 | | | |
|---|---|---|---|
| Storage container | Amber bottle | | |
| | Storage condition | | |
| | 40° C./75% RH | | 25° C./60% RH |
| | Storage duration (in months) | | |
| | Initial | 6 | 6 |
| Description | A Clear colorless solution | | |
| pH | 4.50 | 4.53 | 4.52 |
| Assay of Clonidine HCl (%) | 99.3% | 95.8% | 98.7% |
| Assay of Preservative | 100.4% | 96.7% | 99.7% |
| 4-Hydroxy Clonidine Impurity | ND | ND | ND |
| Any unspecified degradation Product | ND | 0.11 | <LOQ |
| Total Impurities | ND | 0.31 | <LOQ |

TABLE 18

| Composition 012 | | | | | |
|---|---|---|---|---|---|
| Storage container | Amber glass bottle | | HDPE bottle | | |
| | Storage condition | | | | |
| | 40° C./75% RH | 25° C./60% RH | 40° C./25% RH | 25° C./40% RH | |
| | Storage duration (in months) | | | | |
| | Initial | 6 | 6 | 6 | 6 |
| Description | Clear colorless solution | | | | |
| pH | 5.20 | 5.24 | 5.28 | 5.24 | 5.29 |
| Assay of Clonidine HCl | 103.8 | 103.2 | 102.8 | 103.2 | 102.9 |
| Assay of Preservative | 99.6 | 100.0 | 99.8 | 100.4 | 97.2 |

TABLE 18-continued

| Composition 012 | | | | | |
|---|---|---|---|---|---|
| Storage container | Amber glass bottle | | HDPE bottle | | |
| | Storage condition | | | | |
| | 40° C./75% RH | 25° C./60% RH | 40° C./25% RH | 25° C./40% RH | |
| | Storage duration (in months) | | | | |
| | Initial | 6 | 6 | 6 | 6 |
| Related Substances (% impurity) | | | | | |
| 4-Hydroxy Clonidine Impurity | ND | ND | ND | ND | ND |
| Any unspecified Degradation Product | ND | ND | ND | ND | ND |
| Total Impurities | ND | ND | ND | ND | ND |

TABLE 19

| Composition 013 | | | | | |
|---|---|---|---|---|---|
| Storage container | HDPE Container | | | | |
| | Storage Condition | | | | |
| | 40° C./75% RH | 25° C./60% RH | 40° C./25% RH | 25° C./40% RH | |
| | Storage duration (in months) | | | | |
| | Initial | 6 | 6 | 6 | 6 |
| Description | Clear colorless solution | | | | |
| pH | 4.48 | 4.54 | 4.54 | 4.54 | 4.53 |
| Assay of Clonidine HCl | 99.5 | 100.1 | 100.1 | 100.2 | 101.0 |
| Assay of Preservative | 98.4 | 100.6 | 99.3 | 99.5 | 100.5 |
| Related Substances (% impurity) | | | | | |
| 4-Hydroxy Clonidine Impurity | ND | ND | ND | ND | ND |
| Any unspecified Degradation Product | ND | ND | ND | ND | ND |
| Total Impurities | ND | ND | ND | ND | ND |

Composition 012 and 013 both are physically and chemically stable for at least 6 months at all the four stability conditions, without visible particles and with no significant change in assay. Clonidine remains solubilized and compositions were found to be clear without any recrystallization or precipitation.

TABLE 20

| Composition 023 | | | |
|---|---|---|---|
| Storage container | Amber bottle | | |
| | Storage condition | | |
| | 40° C./75% RH | | 25° C./60% RH |
| | Storage duration (in months) | | |
| | Initial | 3 | 3 |
| Description | A Clear colorless solution | | |
| pH | 7.24 | 6.88 | 6.47 |
| Assay of Clonidine HCl (%) | 97.5 | 97.0 | 97.0 |
| Assay of Preservative | 101.5 | 99.6 | 99.8 |
| 4-Hydroxy Clonidine Impurity | ND | ND | ND |
| Any unspecified Degradation Product | ND | ND | ND |
| Total Impurities | ND | ND | ND |

Example 4

Clonidine compositions are set forth in Table 21 below:

TABLE 21

| Ingredients | Composition | | | | | | | | | |
|---|---|---|---|---|---|---|---|---|---|---|
| | 014 | 006 | 015 | 016 | 017 | 018 | 019 | 020 | 021 | 022 |
| | mg/mL | | | | | | | | | |
| Clonidine HCl | 0.02 | 0.02 | 0.02 | 0.02 | 0.02 | 0.02 | 0.02 | 0.02 | 0.02 | 0.02 |
| Potassium sorbate | 1.8 | 0.9 | 1.0 | 1.0 | 1.0 | 1.0 | — | 1.0 | 1.0 | 1.0 |
| Sodium propionate | — | — | — | — | — | — | 0.6 | — | — | — |
| Sodium chloride | 2.9 | 2.9 | 0.02 | 0.04 | 0.1 | 2.5 | 2.5 | 2.5 | 2.5 | 2.5 |
| Sucralose | 0.4 | 0.2 | 0.2 | 0.2 | 0.2 | 0.2 | 0.2 | 0.2 | 0.2 | 0.2 |
| Mixed berry flavor | 2.0 | 1.0 | 0.2 | 0.2 | 0.5 | 0.2 | 0.2 | 0.01 | 0.05 | 0.2 |
| 0.1N HCl | | | q.s. to adjust pH 5.0 to 6.0 | | | | — | | | |
| 0.5N HCl | | | — | | | | q.s. to adjust pH 5.0 to 6.0 | | | |
| Purified water | q.s. | | | | | | | | | |

Manufacturing procedure: Sodium chloride and sucralose were added to a small portion of purified water and stirred continuously at room temperature to get a clear solution. Potassium sorbate/sodium propionate was added to the above solution and mixed to get a clear solution. Next, a flavoring agent was added to the above solution and stirred continuously at room temperature to get a clear solution. The pH of the above solution was adjusted using 0.1 N HCl/0.5N HCl to a pH in the range of 5 to 6. Clonidine was added to the resulting solution under continuous stirring at room temperature to get a clear solution. Purified water was added to make up the final volume. The pH of the solution was checked to ensure it is between 5.0 and 6.0.

TABLE 22

| | Composition 014 | | |
|---|---|---|---|
| | Room temperature 40° C./75% RH 40° C./75% RH | | |
| | Storage duration | | |
| Test | Initial | 1 month | 2 months |
| Pack | HDPE Bottle | | |
| Description | Clear | Clear | Clear |
| pH | 5.51 | 5.47 | 5.53 |
| Assay-Clonidine HCl (%) | 97.1 | 92.3 | 91.8 |
| Assay-Preservative content (%) | 96.7 | 96.1 | 95.9 |
| Related substance | % Impurity | | |
| 4-Hydroxy clonidine Impurity | ND | ND | ND |
| Single maximum unknown impurity | 0 | 0.21 | 0.19 |
| Total Impurities | 0 | 0.41 | 0.58 |

Composition 014 with 0.29% w/w concentration of sodium chloride was physically and chemically stable for at least 2 months without visible particles and with no significant change in assay at 40° C./75% RH. Impurity profile was also found to be satisfactory.

TABLE 23

| | Composition 015 | | | | | |
|---|---|---|---|---|---|---|
| Test | RT | 40° C./75% RH | 25° C./60% RH | 40° C./25% RH | 25° C./40% RH | 40° C./75% RH (Inverted) |
| Storage duration | Initial | 1 month | | | | |
| Pack | | HDPE Bottle | | | | |
| Description | Clear | Clear | Clear | Clear | Clear | Clear |
| pH | 5.63 | 5.69 | 5.63 | 5.66 | 5.66 | 5.71 |
| Assay-Clonidine HCl (%) | 99.7 | 97.7 | 95.3 | 94.0 | 95.8 | 96.2 |
| Assay-Preservative content (%) | 100.2 | 98.0 | 98.5 | 98.2 | 98.8 | 97.5 |
| Related substance | | % Impurity | | | | |
| 4-Hydroxy clonidine Impurity | ND | ND | ND | ND | ND | ND |
| Single maximum unknown impurity | 0.04 | 0.33 | 0.37 | 0.38 | 0.33 | 0.37 |
| Total Impurities | 0.04 | 0.74 | 0.77 | 0.80 | 0.66 | 0.86 |

RT = Room Temperature

Composition 015 was physically and chemically stable for at least 1 month without visible particles and with no significant change in assay at 40° C./75% RH, 25° C./60% RH, 40° C./25% RH, 25° C./40% RH and at 40° C./75% RH (Inverted) conditions. Impurity profile was also found to be satisfactory.

TABLE 24

| | | Composition 016 | | | | |
|---|---|---|---|---|---|---|
| Test | Room temperature | 40° C./ 75% RH | 25° C./ 60% RH | 40° C./ 25% RH | 25° C./ 40% RH | 40°° C./ 75% RH (Inverted) |
| Storage duration | Initial | | | 1 month | | |
| Pack | | | | HDPE Bottle | | |
| Description | Clear | Clear | Clear | Clear | Clear | Clear |
| pH | 5.63 | 5.63 | 5.59 | 5.61 | 5.6 | 5.62 |
| Assay-Clonidine HCl (%) | 99.8 | 96 | 95.9 | 95.2 | 95.6 | 92.7 |
| Assay-Preservative content (%) | 102.2 | 97.4 | 99 | 97.3 | 99 | 98.6 |
| Related substance | | | % Impurity | | | |
| 4-Hydroxy clonidine Impurity | ND | ND | ND | ND | ND | ND |
| Single maximum unknown impurity | 0.02 | 0.4 | 0.42 | 0.5 | 0.46 | 0.31 |
| Total Impurities | 0.02 | 0.86 | 0.75 | 1.01 | 0.80 | 0.78 |

Composition 016 was physically and chemically stable for at least 1 month without visible particles and with no significant change in assay at 40° C./75% RH, 25° C./60% RH, 40° C./25% RH, 25° C./40% RH and at 40° C./75% RH (Inverted) conditions. Impurity profile was also found to be satisfactory.

TABLE 25

| | | Composition 017 | | | | |
|---|---|---|---|---|---|---|
| Test | RT | 40° C./ 75% RH | 25° C./ 60% RH | 40° C./ 25% RH | 25° C./ 40% RH | 40° C./ 75% RH (Inverted) |
| Storage duration | Initial | | | 1 month | | |
| Pack | | | | HDPE Bottle | | |
| Description | Clear | Clear | Clear | Clear | Clear | Clear |
| pH | 5.63 | 5.68 | 5.59 | 5.68 | 5.62 | 5.7 |
| Assay-Clonidine HCl (%) | 99.4 | 97.4 | 97.9 | 96.3 | 97.5 | 96.7 |
| Assay-Preservative content (%) | 100.2 | 98.5 | 99.1 | 98.2 | 99.3 | 98.8 |
| Related substance | | | % Impurity | | | |
| 4-Hydroxy-clonidine Impurity | ND | ND | ND | ND | ND | ND |
| Single maximum unknown impurity | 0.01 | 0.19 | 0.2 | 0.21 | 0.19 | 0.18 |
| Total Impurities | 0.01 | 0.35 | 0.34 | 0.44 | 0.34 | 0.51 |

RT = Room Temperature

Composition 017 was physically and chemically stable for at least 1 month without visible particles and with no significant change in assay at 40° C./75% RH, 25° C./60% RH, 40° C./25% RH, 25° C./40% RH and at 40° C./75% RH (Inverted) conditions. Impurity profile was also found to be satisfactory.

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

The invention claimed is:

1. A liquid pharmaceutical composition having extended stability, said composition consisting of:
    (a) clonidine hydrochloride at a concentration of about 20 g/mL;
    (b) sodium chloride as a stabilizer at a concentration of about 2.5 mg/mL;
    (c) a preservative at a concentration of about 0.01% to 5.0%;
    (d) a sweetener at a concentration of about 0.20 mg/mL;
    (e) a flavoring agent at a concentration of about 0.20 mg/mL; and
    (f) water; and
    (g) optionally, a pH adjusting agent;
    wherein said composition is free of buffer;
    wherein said composition is contained in a multi-dose container;
    wherein said composition is an oral solution; and
    wherein not more than 2% w/w of total impurities are formed when said composition is stored for at least 6 months at 25° C./40% RH or 25° C./60% RH or 40° C./25% RH or 40° C./75% RH.

2. The composition of claim 1, wherein said composition has a pH in a range from about 4 to about 8.

3. The composition of claim 1, wherein said composition has a pH in a range from about 5 to about 6.

4. A liquid pharmaceutical composition having extended stability, said composition consisting of:
   (a) clonidine hydrochloride at a concentration of about 20 g/mL;
   (b) sodium chloride as a stabilizer at a concentration of about 2.5 mg/mL;
   (c) a preservative at a concentration of about 0.01% to 5.0%, wherein the preservative is potassium sorbate and/or sodium propionate;
   (d) a sweetener at a concentration of about 0.20 mg/mL;
   (e) a flavoring agent at a concentration of about 0.20 mg/mL;
   (f) water;
   (g) optionally, a pH adjusting agent;
   wherein said composition is free of buffer;
   wherein said composition is an oral solution; and
   wherein not more than 2% w/w of total impurities are formed when said composition is stored for at least 6 months at 25° C./40% RH or 25° C./60% RH or 40° C./25% RH or 40° C./75% RH.

5. The composition of claim 1, wherein said composition is provided in a polyethylene terephthalate (PET) bottle.

6. The composition of claim 1, wherein said composition is provided in a high-density polyethylene (HDPE) bottle.

7. The composition of claim 1, wherein said composition is provided in a glass bottle.

8. The composition of claim 1, wherein said composition exhibits in-use shelf life of at least one month when stored at room temperature.

9. The composition of claim 1, wherein the preservative is potassium sorbate.

10. The composition of claim 1, wherein the preservative is sodium propionate.

11. The composition of claim 1, wherein the sweetener is sucralose.

12. The composition of claim 1, wherein the pH is from about 3 to about 9.

13. The composition of claim 1, wherein the pH is from about 4 to about 6.

14. The composition of claim 4, wherein the preservative is potassium sorbate.

15. The composition of claim 4, wherein the preservative is sodium propionate.

16. The composition of claim 4, wherein the sweetener is sucralose.

17. The composition of claim 4, wherein the pH is from about 3 to about 9.

18. The composition of claim 4, wherein the pH is from about 4 to about 6.

19. The composition of claim 4, wherein the pH is from about 5 to about 6.

20. The composition of claim 4, wherein the pH is from about 4 to about 8.

21. The composition of claim 4, wherein the composition exhibits in-use shelf-life for at least one month when stored at room temperature.

22. The composition of claim 1, wherein the preservative is present at a concentration of 2.5 mg/mL.

23. The composition of claim 4, wherein the preservative is present at a concentration of 2.5 mg/mL.

* * * * *

UNITED STATES PATENT AND TRADEMARK OFFICE
CERTIFICATE OF CORRECTION

PATENT NO. : 12,233,049 B2
APPLICATION NO. : 17/866115
DATED : February 25, 2025
INVENTOR(S) : Shailendra Mandge et al.

Page 1 of 1

It is certified that error appears in the above-identified patent and that said Letters Patent is hereby corrected as shown below:

In the Claims

In Claim 1, at Column 33, Lines 66-67:
"(a) clonidine hydrochloride at a concentration of about 20g/mL;" should read --(a) clonidine hydrochloride at a concentration of about 20µg/mL;--.

In Claim 4, at Column 35, Lines 3-4:
"(a) clonidine hydrochloride at a concentration of about 20g/mL;" should read --(a) clonidine hydrochloride at a concentration of about 20µg/mL;--.

Signed and Sealed this
Fifth Day of August, 2025

Coke Morgan Stewart
*Acting Director of the United States Patent and Trademark Office*